United States Patent
Yu

(10) Patent No.: US 10,292,769 B1
(45) Date of Patent: May 21, 2019

(54) SURGICAL ASSISTIVE DEVICE AND METHOD FOR PROVIDING ASSISTANCE IN SURGERY OF ANATOMICAL PORTIONS OF INTERNAL ORGAN AFFECTED BY INTRAOPERATIVE SHIFT

(71) Applicant: SONY CORPORATION, Tokyo (JP)

(72) Inventor: Liangyin Yu, San Jose, CA (US)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 16/056,883

(22) Filed: Aug. 7, 2018

(51) Int. Cl.
| | |
|---|---|
| *A61B 34/10* | (2016.01) |
| *A61B 90/00* | (2016.01) |
| *A61B 5/00* | (2006.01) |
| *G06T 7/00* | (2017.01) |

(Continued)

(52) U.S. Cl.
CPC ............ *A61B 34/10* (2016.02); *A61B 5/0013* (2013.01); *A61B 34/20* (2016.02); *A61B 90/361* (2016.02); *G06T 7/0014* (2013.01); *G06T 7/593* (2017.01); *A61B 2034/107* (2016.02); *A61B 2034/2057* (2016.02); *A61B 2034/2065* (2016.02); *A61B 2090/371* (2016.02); *A61B 2090/373* (2016.02); *A61B 2576/00* (2013.01); *G06T 2207/10012* (2013.01); *G06T 2207/10056* (2013.01); *G06T 2207/30008* (2013.01); *G06T 2207/30016* (2013.01); *G06T 2207/30096* (2013.01); *G06T 2207/30101* (2013.01)

(58) Field of Classification Search
CPC ..... A61B 34/20; A61B 90/361; A61B 5/0013; G06T 7/593; G06T 7/0014
See application file for complete search history.

(56) References Cited

U.S. PATENT DOCUMENTS

| | | | |
|---|---|---|---|
| 8,768,022 B2 | 7/2014 | Miga et al. | |
| 9,008,381 B2 | 4/2015 | Bucki et al. | |
| 9,336,592 B2 | 5/2016 | Fan et al. | |
| (Continued) | | | |

FOREIGN PATENT DOCUMENTS

WO   2011/143820 A1   11/2011

OTHER PUBLICATIONS

Dumpuri, et al., "A Fast and Efficient Method to Compensate for Brain Shift for Tumor Resection Therapies Measured Between Preoperative and Postoperative Tomograms", Feb. 17, 2010, 13 pages.

*Primary Examiner* — Edward Park
(74) *Attorney, Agent, or Firm* — Chip Law Group

(57) ABSTRACT

Various aspects of a surgical assistive device and method to provide assistance in neurosurgery are disclosed herein. The surgical assistive device includes circuitry that determines initial positional shift in the anatomical portion of a subject caused by an incision into a protective portion. A first depth value is estimated based on the plurality of stereo images that are captured from different specified positions of the surgical image capture device to capture views of the anatomical surface of the anatomical portion through the incision. A residual shift in a position of a surgical region of interest is determined with respect to the estimated first depth value. Surgical guidance information is generated to indicate a correct depth of the surgical region of interest in a surgical cavity, based on the determined residual shift. Display of the generated surgical guidance information is controlled on a display screen coupled to the surgical assistive device.

17 Claims, 6 Drawing Sheets

(51) Int. Cl.
*G06T 7/593* (2017.01)
*A61B 34/20* (2016.01)

(56) References Cited

U.S. PATENT DOCUMENTS

| | | | |
|---|---|---|---|
| 2007/0198022 A1* | 8/2007 | Lang | A61B 17/154 |
| | | | 606/88 |
| 2008/0058593 A1* | 3/2008 | Gu | G06T 7/0012 |
| | | | 600/109 |
| 2008/0243127 A1* | 10/2008 | Lang | A61B 5/4528 |
| | | | 606/87 |
| 2016/0143693 A1* | 5/2016 | Yilmaz | B25J 9/1664 |
| | | | 600/424 |

* cited by examiner

SURGICAL ASSISTIVE DEVICE AND METHOD FOR PROVIDING ASSISTANCE IN SURGERY OF ANATOMICAL PORTIONS OF INTERNAL ORGAN AFFECTED BY INTRAOPERATIVE SHIFT

CROSS-REFERENCE TO RELATED APPLICATIONS/INCORPORATION BY REFERENCE

None.

FIELD

Various embodiments of the disclosure relate to medical imaging technologies and computer-assisted surgery technologies. More specifically, various embodiments of the disclosure relate to a surgical assistive device and method for providing assistance in surgery of anatomical portions of an internal organ, which is affected by intraoperative shift.

BACKGROUND

Advancements in the field of medical imaging have paved way to automate and provide real time assistance in surgical processes that are often complex and performed manually by surgeons. In one such process, during surgery, an internal organ, such as the brain of a subject may suffer an inevitable deformation that may be caused by initial brain shift due to expulsion of brain fluid, followed by, for example, a resection deformation. One of the primary causes of deformation is the intraoperative brain shift that is caused by tissue deformation that happens while the surgeon tries to operate on a target brain tissue in an exposed region of the brain. The effect of deformation on the exposed region of the brain causes difficulty in localization of the target brain tissue during the surgery with respect to pre-determined tissue positions obtained prior to the surgery (i.e. during pre-operative imaging). During surgery, such deformation may therefore lead a surgeon to a tissue that is different from a target tissue or may lead to inaccurate assumptions in positioning of the target tissue among different surgeons.

In medical practice, surgeons usually compensate for deformation of brain tissue based on their prior experience with similar surgical procedures. However, a mere assumption while compensating for deformation based on prior experience may affect accuracy and precision of the surgical procedure. Also, the precision with which the surgical procedure may be performed greatly depends on the experience level of the surgeon and therefore, an improved solution is required that may assist a surgeon in estimating precise intraoperative brain shift caused by tissue deformation during surgery.

Further limitations and disadvantages of conventional and traditional approaches will become apparent to one skilled in the art, through comparison of described systems with some aspects of the present disclosure, as set forth in the remainder of the present application and with reference to the drawings.

SUMMARY

A surgical assistive device and method is described for providing assistance in surgery of anatomical portions of an internal organ, which is affected by an intraoperative shift, as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

Certain embodiments of the disclosure may be found in a surgical assistive device and method for assistance in surgery of anatomical portions (e.g., occipital lobe, temporal lobe, etc.) of an internal organ (e.g., brain), which is affected by an intraoperative shift. Various embodiments of the disclosure may provide a surgical assistive device, which may include a surgical image capture device (e.g., a stereo microscope) and a shift compensation circuitry communicatively coupled to the surgical image capture device. The surgical image capture device may be configured to capture a plurality of stereo images of the anatomical portion of a body of a subject (e.g., a human subject). The anatomical portion may be a defined portion of an internal organ exposed to the surgical image capture device post an incision of a protective portion (e.g., skull) that encloses the internal organ. The surgical assistive device may optimally model different intraoperative shifts caused in the anatomical portion of an internal organ (e.g., caused by tissue deformation) when different regions of the anatomical portion are subjected to a surgery. The disclosed surgical assistive device models different intraoperative shifts that may be caused by tissue deformation of the brain, which in turn helps a surgeon to perform the surgery with precision and removes a bias (which was conventionally present due to experience-based intraoperative shift assumptions by surgeons) to an overall surgical procedure. The surgical assistive device ensures precise guidance information that may include visualizations that indicate a residual shift (i.e., intraoperative shift). Further, the surgical assistive device may generate and provide guidance for the surgeon for a simplified localization of a target tissue of the anatomical portion during the surgery (i.e., during intra-operative stage) with respect to pre-determined tissue positions obtained prior to the surgery. (i.e., during pre-operative stage). In surgery, the surgical assistive device may generate output surgical guidance information on a display screen coupled to the surgical assistive device such that navigation of a surgical instrument to the target tissue (e.g., a surgical region of interest) is accurately facilitated. This enables a surgeon to correctly determine intraoperative brain shift caused by tissue deformation during surgery, and thereby localize the target tissue in a surgical cavity.

Figure 1:
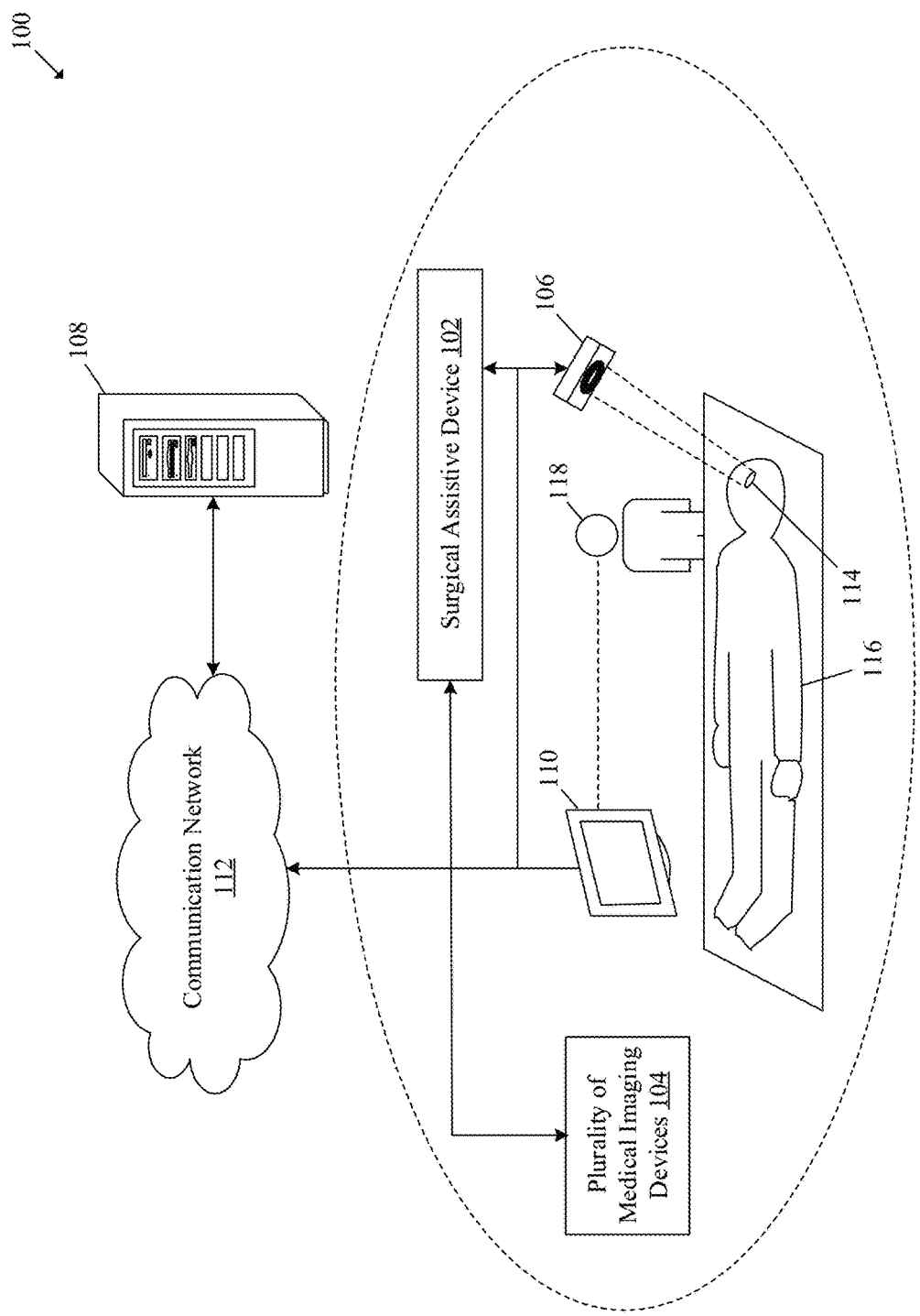
FIG. 1 is a diagram that illustrates a network environment for providing assistance for surgery of anatomical portions of an internal organ, which is affected by an intraoperative shift, in accordance with an embodiment of the disclosure.

FIG. 1 illustrates a network environment for providing assistance for surgery of anatomical portions of an internal organ, which is affected by an intraoperative shift, in accordance with an embodiment of the disclosure. With reference to FIG. 1, there is shown a network environment 100 that may include a surgical assistive device 102, a plurality of medical imaging devices 104, a surgical image capture device 106, and a medical data server 108. In some embodiments, a display screen 110 may be integrated with the surgical assistive device 102. In some embodiments, the display screen 110 may be communicatively coupled to the surgical assistive device 102 as a peripheral device. In accordance with an embodiment, the surgical assistive device 102 may be communicatively coupled to the surgical image capture device 106 and the medical data server 108, via a communication network 112. There is further shown an anatomical portion 114 of an internal organ of a subject, such as the human subject 116, and a user, such as a surgeon 118 or a surgical assistant, associated with the surgical assistive device 102.

The surgical assistive device 102 may comprise suitable logic, circuitry, and interfaces that may be configured to determine a residual shift (i.e., an intraoperative shift) in a position of a surgical region of interest in the anatomical portion 114 of the human subject 116, with respect to a known position of a surgical region of interest. The residual shift may be a part of information that is generated to assist the surgeon 118, to perform the surgery in the anatomical portion 114 of the human subject 116. The surgical assistive device 102 may provide a real-time or a near real-time assistance to the surgeon 118 in an event of the tissue deformation of the anatomical portion 114 during surgery. Examples of the surgical assistive device 102 may include, but are not limited to, a specialized medical-grade machine, computer-assisted surgical system or a robot-assisted surgical system. In some embodiments, the surgical assistive device 102 may be integrated inside a medical equipment or machine as an embedded device, e.g., an MRI or an X-ray system. In some embodiments, surgical assistive device 102 may be a computing device that may also be integrated with a display device. Examples of the surgical assistive device 102 may include, but are not limited to an intra-operation Magnetic Resonance Imaging (MRI), open MRI devices, Computed Tomography (CT) scanners, or Positron Emission Tomography (PET).

The plurality of medical imaging devices 104 may correspond to a medical examination equipment (e.g., pre-surgical or intra-operative examinations) that generates visual representations of internal structures or anatomical portions, such as the anatomical portion 114, of the human subject 116. Such visual representations of the internal structures or the anatomical portions may be generated for clinical analysis and medical intervention when the human subject 116 is in a preoperative state or an intraoperative state. The plurality of medical imaging devices 104 may be multimodal sources (e.g., sources of MRI data, CT scan data, PET data, open CT data, etc.). The multimodal sources may be used to obtain datasets related to the anatomical portion 114. Examples of the plurality of medical imaging devices 104 may include, but are not limited to, an X-ray computed tomography (CT) scanner, a magnetic resonance imaging (MRI) scanner, a magnetic resonance angiography (MRA) scanner, a fluid-attenuated inversion recovery (FLAIR) based scanner, and/or a positron emission tomography (PET) scanner.

The surgical image capture device 106 may be a digital stereoscopic microscope that is affixed to a precision stereoscopic camera. The surgical image capture device 106 may be configured to capture and generate three dimensional (3D) stereoscopic images or 3D-structure data for an anatomical portion, such as the anatomical portion 114, of the human subject 116. A plurality of images may be acquired from different viewpoints in space to generate the 3D stereoscopic images or 3D-structure data of the anatomical portion 114 in an intraoperative state. The plurality of images, such as stereo image pairs, may be acquired by use of multiple cameras from different viewpoints, multiple camera lenses of a single stereo camera, or a single moving camera. Alternatively, the surgical assistive device 102 may be communicatively coupled to the surgical image capture device 106, via the communication network 112. Examples of the surgical image capture device 106 may include, but are not limited to, a stereo microscope, a stereo camera and a surgical camera. Also, in some cases, the surgical image capture device 106 may be mounted on (or integrated with) a surgical microscope used to perform microsurgery/surgery.

The medical data server 108 may comprise suitable logic, circuitry and interfaces that may be configured to transmit one or more pre-stored datasets of imaging data to the surgical assistive device 102, via the communication network 112. The one or more pre-stored datasets of imaging data may correspond to the imaging data of the anatomical portion 114 measured in the preoperative state, prior to a tissue deformation in the anatomical portion 114. The one or more pre-stored datasets may also correspond to multimodal images (e.g., data from MRI, CT scan, PET, open CT).

In accordance with an embodiment, the medical data server 108 and the surgical assistive device 102 may be integrated as a computer-assisted surgical system. Both the medical data server 108 and the surgical assistive device 102 may be part of a computer-assisted surgical system. In some embodiments, the medical data server 108 may be implemented through a plurality of cloud-based resources by use of several technologies that are well known to those skilled in the art. In other embodiments, the functionalities of the medical data server 108 may be implemented by the surgical assistive device 102, without a departure from the scope of the disclosure. The medical data server 108 may include at least one of a cloud storage, a virtual cloud storage, or an on premise data storage. The medical data server 108 may be compliant with one or more standards or laws, for example, Health Insurance Portability and Accountability Act (HIPAA).

The display screen 110 may comprise suitable logic, circuitry, and interfaces that may be configured to display surgical guidance information that may be generated by the surgical assistive device 102. The surgical assistive device 102 may be further configured to render, on display screen 110, the surgical guidance information of the anatomical portion 114 during the surgery. The display screen 110 may be updated with the surgical guidance information of the anatomical portion 114 in accordance with a real time or a near-real time deformation of tissues of the anatomical portion 114. The tissue may be deformed post incision into a protective portion of the internal organ during surgery. The display screen 110 may be part of different devices, such as a smartphone. The display screen 110 may also be a part of a portable electronic device, a wearable electronic device, a non-portable electronic device, or medical devices inside an operation theatre where the human subject 116 may undergo a surgery. A user, such as the surgeon 118, of the display screen 110 may operate the surgical assistive device 102, with visual support, instructions, and/or guidance from a user-interface of the display screen 110.

The communication network 112 may include a medium through which the surgical assistive device 102, the surgical image capture device 106, and/or the medical data server 108 may communicate with each other. The communication network 112 may be a wired or wireless communication network. Examples of the communication network 112 may include, but are not limited to, a Local Area Network (LAN), a Wireless Local Area Network (WLAN), a cloud network, a Long Term Evolution (LTE) network, a plain old telephone service (POTS), a Metropolitan Area Network (MAN), and/or the Internet. Various devices in the network environment 100 may be configured to connect to the communication network 112, in accordance with various wired and wireless communication protocols. Examples of such wired and wireless communication protocols may include, but are not limited to, Transmission Control Protocol and Internet Protocol (TCP/IP), User Datagram Protocol (UDP), Hypertext Transfer Protocol (HTTP), File Transfer Protocol (FTP), ZigBee, EDGE, infrared (IR), IEEE 802.11, 802.16, cellular communication protocols, and/or Bluetooth (BT) communication protocols.

In operation, a user (e.g., the surgeon 118) may utilize the surgical assistive device 102 to perform a surgical or diagnostic procedure on the anatomical portion 114 of the human subject 116. The anatomical portion 114 may be a portion of an internal organ that is enclosed by a protective portion (e.g., a skull or a cranium that encloses the brain). The anatomical portion 114 (e.g., parietal lobe, frontal lobe, temporal lobe, or occipital lobe, etc.) is a portion of the internal organ, which is exposed after an incision into the protective portion that encloses the internal organ. Alternatively stated, the anatomical portion 114 may be a portion of the internal organ which is exposed during surgery after removal of a portion of the protective portion. The surgeon 118 may specify a plurality of surgical region of interests in the anatomical portion 114. Each surgical region of interest may be associated with different material properties based on different types of tissues that are present in the anatomical portion. The material properties may include a tensile elasticity value (e.g., Young's modulus) and a tissue density (e.g. measured in $kg/m^3$) associated with a type of tissue in the anatomical portion 114.

In some embodiments, the anatomical portion 114 may be a portion of the brain (or the cerebrum), or at least a brain portion of the human subject 116. The anatomical portion 114 may be exposed to the surgical image capture device 106 and the surgeon 118, after an incision or a removal of a portion (e.g., a parietal bone, an occipital bone, a temporal bone, or a frontal bone, etc.) of the skull (or the cranium) of the human subject 116. In such embodiments, the plurality of surgical region of interests may be a brain tissue, a network of blood vessels, and brain ventricles present in the anatomical portion 114. The plurality of surgical region of interests may further include a tumor structure (e.g., malignant or benign tissues) within the brain of the human subject 116.

The surgical assistive device 102 may be configured to retrieve at least a dataset of pre-operative multimodal images, associated with the anatomical portion 114, from the medical data server 108. In certain embodiments, the dataset of pre-operative multimodal images may be retrieved, by the surgical assistive device 102, directly from the plurality of medical imaging devices 104. The dataset may include a plurality of 2D images that represents slice planes through a volume of the anatomical portion 114, such as slices through the skull of the human subject 116. The dataset may correspond to MRI data set taken prior to surgery of the internal organ in a preoperative state. The surgical assistive device 102 may be configured to register the retrieved dataset associated with the anatomical portion 114, in an image-guided neurosurgical system (IGNS) or other imaging systems. The IGNS may be part of the surgical assistive device 102 or receive inputs, associated with shifts caused by different types of deformations in the anatomical portion 114, externally from the surgical assistive device 102. In such cases, the IGNS may update visual models of the anatomical portion 114 (or the internal organ) to highlight the information that is received as inputs from the surgical assistive device 102.

The multimodal sources may be medical imaging devices 104 that may utilize different imaging techniques, which may include, but are not limited to, Magnetic Resonance Imaging (MRI), Computed Tomography (CT), Positron Emission Tomography (PET), Fluid Attenuated Inversion Recovery (FLAIR), and Magnetic Resonance Angiography (MRA) based medical imaging techniques. Such different techniques may be utilized to acquire a plurality of datasets that exemplifies different characteristics of the anatomical portion 114 and/or adds resolution to the measurement of the anatomical portion 114.

The surgical assistive device 102 may be configured to determine a first position of an anatomical surface (e.g., an exposed surface of the anatomical portion 114) associated with the anatomical portion 114, prior to incision into the protective portion of the internal organ. The first position may be determined based on the retrieved dataset of pre-operative multimodal images from different multimodal sources (e.g., an MRI scanner). Thereafter, in some cases, the surgical assistive device 102 may be configured to retrieve material parameters, associated with a type of tissue (or different types of tissues) exposed after incision in the anatomical portion 114, from the medical data server 108. The material parameters may include tensile elasticity values for a type of tissue in the anatomical portion 114 and a tissue density associated with the type of tissue.

In the intraoperative state, at a time when a portion of the protective portion is removed in the surgery (prior to resection), the anatomical portion 114 (or sometimes the entire internal organ) may undergo a sudden loss of fluid (e.g., cerebrospinal fluid) around different tissues of the anatomical portion 114 (or the internal organ). The sudden loss of fluid may lead to a shift in an anatomical surface of the anatomical portion 114 that is exposed after the incision. Alternatively, the exposed anatomical surface may deform (uniformly or non-uniformly across the anatomical surface) after the sudden loss of fluid. Such loss may further occur continuously (or in a discontinuous manner) during a resection procedure.

In order to measure the deformation caused by sudden loss of fluid, the surgical image capture device 106 may be configured to determine an initial positional shift of the anatomical surface (e.g., outer surface of temporal lobe in the brain) of the anatomical portion 114. The initial positional shift of the anatomical surface may be caused by the incision into the protective portion. The initial positional shift of an anatomical surface of the anatomical portion 114 may be determined from the first position of the anatomical surface to a second position of the anatomical surface. The first position may correspond to a position of the anatomical surface enclosed by the protective portion in the pre-operative state that occurs prior to the incision and the second position may correspond to a position of the anatomical surface in the intra-operative state that occurs post the incision. The plurality of stereo images of the anatomical portion 114 may be captured by the surgical image capture device 106.

In order to determine the second position of the anatomical surface in the intraoperative state, the surgical assistive device 102 may be configured to utilize stereo vision of the surgical image capture device 106, to determine the second position of the an initial positional shift of an anatomical surface of the anatomical portion 114. Thereafter, the initial positional shift may be determined based on a comparison of a pre-operative depth value associated with the first position of the anatomical surface with a corresponding depth value of the anatomical surface at the second position. The first position may be estimated, from pre-operative multimodal images of the internal organ in the registered dataset, in the pre-operative state and the second position may be estimated based on the captured plurality of stereo images.

In the intraoperative state, different tissues in the anatomical portion 114 may further deform due to different factors, for example, different levels of complexity of a tissue structure in the anatomical portion 114, effects of gravitational forces, and/or further loss of fluid, such as the cerebrospinal fluid, around the anatomical portion 114 when the tissue (or the anatomical portion 114) is exposed in the intraoperative state. Such factors may also include an extent of softness of different tissues in the anatomical portion 114, systolic/diastolic blood pressure, and/or an extent of displacement of a protective portion or a supportive structure associated with the anatomical portion 114 in the surgery.

In certain embodiments, the anatomical portion 114 (or the internal organ) may further suffer deformations (referred to as resection deformations) while the resection procedure is performed (by the surgeon 118) on the anatomical portion 114 using a surgical instrument. The resection deformation may occur when the surgeon 118 guides the surgical instrument through a surgical cavity to resect a specific tissue(s) from a surgical region of interest in the anatomical portion 114. The tissue deformation (or resection deformation) may also cause displacement of certain anatomical tissue structures, and therefore a depth (previously estimated by the surgeon 118 in the pre-operative state) by which the surgical instrument may be guided to access (and/or perform resection on) a surgical region of interest through a surgical cavity, may undergo modifications during the surgery.

The surgical assistive device 102 may need to model the effects of such deformations and associated modifications to the depth. The initial positional shift may only be one of the several parameters that may contribute to the overall intraoperative shift of the anatomical portion 114. The surgical assistive device 102 may be further configured to utilize the stereo vision of the surgical image capture device 106, to estimate a first depth value from the second position of the anatomical surface to a surgical region of interest present at a bottom of a surgical cavity in the anatomical portion 114 The first depth value may be an apparent depth estimated based on the plurality of stereo images that are captured from different specified positions of the surgical image capture device 106 to capture views of the anatomical surface of the anatomical portion 114, obtained post the incision.

As the first depth value is estimated from the second position, the estimation of the first depth value takes into account the contributions of the initial positional shift (e.g., the initial intraoperative brain shift) that is caused by sudden loss of fluid. However, the first depth value may be estimated without taking into account the effect of tissue deformation. The effect of tissue deformations (or resection deformation) may be similar to the contributions of the initial positional shift. For example, the initial positional shift of the anatomical surface may be "10 mm" and similarly, a shift in a depth of a surgical cavity caused by tissue deformation may be "6 mm". Such values may vary based on a type of surgical procedure and an area of the anatomical surface that is exposed after incision. Therefore, the surgical image capture device 106 may be configured to determine a residual shift in a position of the surgical region of interest with respect to the estimated first depth value. The residual shift may be determined such that a deviation in the estimation of the first depth value caused by tissue deformation in the anatomical portion 114, may be compensated by the determined residual shift with respect to a second depth value of the surgical region of interest in the surgical cavity. The residual shift may be determined based on a first relationship model of material parameters associated with a type of tissue in the anatomical portion 114 and the estimated first depth value. The first relationship model may be a polynomial expansion of a multivariate relationship among at least the material parameters, the determined initial positional shift of the anatomical surface, orientation information associated with the surgical instrument, and the estimated first depth value. The second depth value of surgical region of interest in surgical cavity may be determined by the surgical assistive device 102 based on the second relationship model. The second relationship model may be obtained by a polynomial expansion of a multivariate relationship among at least the material parameters, the determined initial positional shift of the anatomical surface, orientation information associated with the surgical instrument, and the estimated first depth value.

In order to assist the surgeon 118, the surgical assistive device 102 may be configured to generate surgical guidance information that includes an amount of depth that should be compensated from the first depth value to the second depth value, to indicate a correct depth of the surgical region of interest in the surgical cavity, based on the determined residual shift. Alternatively stated, the surgical guidance information may indicate a depth by which a surgical instrument may be displaced vertically in the surgical cavity to reach a correct depth and to an actual position of the surgical region of interest. The precise guidance information may be utilized by the surgeon 118 to compensate for the effect of the intraoperative shift of the anatomical portion 114 during the surgical procedure.

In certain embodiments, the surgical assistive device 102 is further configured to generate a three dimensional (3D) graphic model of the anatomical portion 114. The generation of the 3D graphic model of the anatomical portion 114 may be based on the determined initial positional shift of the anatomical surface, the estimated first depth value, the determined residual shift, and the determined second depth value of the surgical cavity. The generation of the 3D graphic model of the anatomical portion 114 may be further based on the registered dataset of pre-operative multimodal images received from multimodality sources.

The surgical assistive device 102 may be configured to control display of a plurality of multi-dimensional graphical views of the anatomical portion 114 (after the deformation). Such generation and display of the plurality of multi-dimensional graphical views of the anatomical portion 114 in the presence of the tissue deformation may assist the surgeon 118 in real-time or near real-time to perform a surgery on the anatomical portion 114. The plurality of multi-dimensional graphical views may be user-controlled, modified, and visualized as per a medical requirement. The detailed operation of the surgical assistive device 102 is further described, for example, in FIG. 2.

In some embodiments, the disclosed surgical assistive device 102 may also be used to provide assistance during a surgery of different anatomical portions of different animal subjects. The anatomical portions may be a portion of the brain, heart, or other internal organs, which may be affected by tissue deformations and/or may undergo intraoperative shift.

Figure 2:
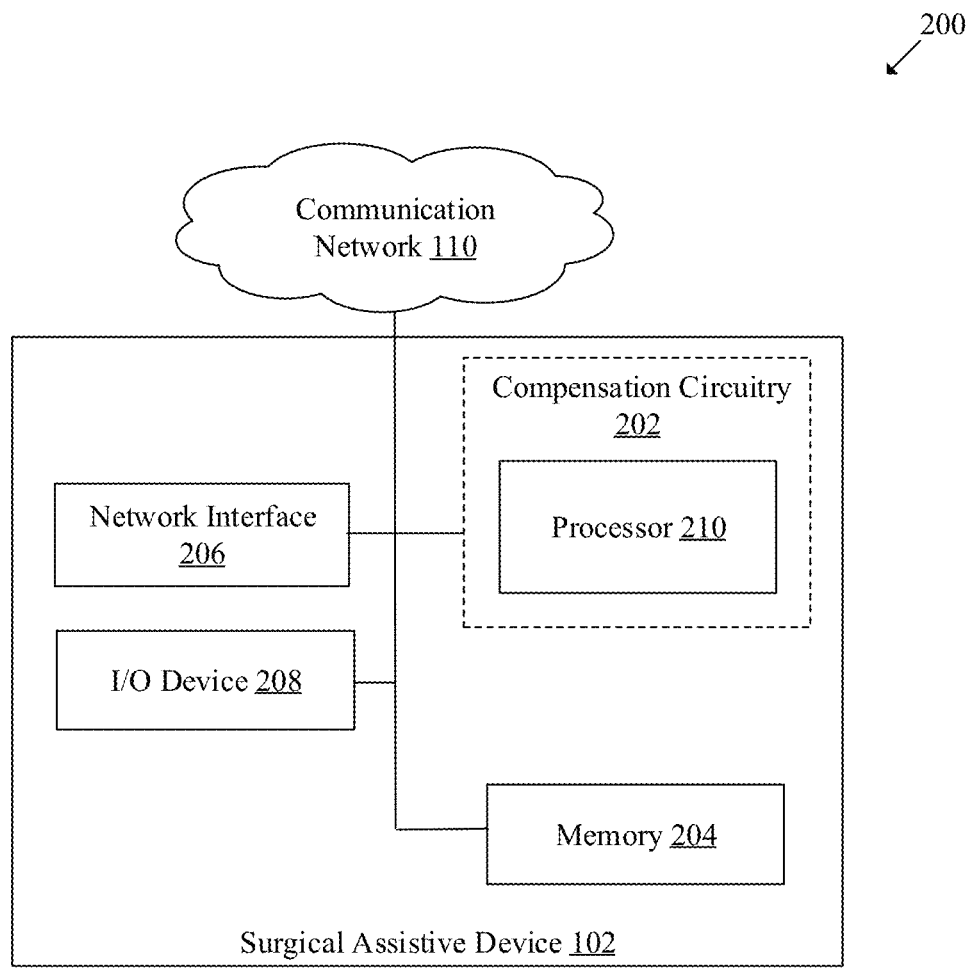
FIG. 2 illustrates a block diagram of an exemplary surgical assistive device that assists in surgery of anatomical portions of an internal organ, which is affected by an intraoperative shift, in accordance with an embodiment of the disclosure.

FIG. 2 illustrates a block diagram of an exemplary surgical assistive device that assists in surgery of anatomical portions of an internal organ, which is affected by an intraoperative shift, in accordance with an embodiment of the disclosure. FIG. 2 is explained in conjunction with elements from FIG. 1. With reference to FIG. 2, there is shown the surgical assistive device 102. The surgical assistive device 102 may include one or more circuitries, such as a compensation circuitry 202, a memory 204, a network interface 206, one or more input/output (I/O) devices, such as an I/O device 208. The compensation circuitry 202 may include a processor 210. The compensation circuitry 202 may be communicatively coupled to the memory 204, the network interface 206, and the I/O device 208. Also, the network interface 206 may communicate with the one or more medical data servers, such as the medical data server 108, via the communication network 112 under the control of the compensation circuitry 202.

The compensation circuitry 202 may comprise suitable logic, circuitry, and interfaces that may be configured to render guidance information that facilitates a surgeon (e.g., the surgeon 118) to compensate for an intraoperative shift (i.e., a residual shift) caused by deformation of the anatomical portion 114 of an internal organ of the human subject 116. Based on the rendered guidance information, the surgeon 118 may move the surgical instrument at a correct depth inside a surgical cavity within the anatomical portion 114. In some embodiments, the compensation circuitry 202 may be implemented based on different processor technologies known in the art. Examples of the compensation circuitry 202 may be an x86-based processor, x86-64-based processor, a Reduced Instruction Set Computing (RISC) processor, an Application-Specific Integrated Circuit (ASIC) processor, a Complex Instruction Set Computing (CISC) processor, a central processing unit (CPU), an Explicitly Parallel Instruction Computing (EPIC) processor, a Very Long Instruction Word (VLIW) processor, and/or other processors or circuits.

The memory 204 may comprise suitable logic, circuitry, and/or interfaces that may be configured to store a set of instructions executable by the compensation circuitry 202. The memory 204 may be configured to store dataset of one or more material properties associated with a type of tissue of a surgical region of interest of the anatomical portion 114. The dataset may be retrieved from the medical data server 108 and stored in the memory 204. The memory 204 may be further configured to store a plurality of stereo images captured by the surgical image capture device 106. The memory 204 may be configured to store information from one or more patient profiles associated with physiological data or medical history of the subject, such as the human subject 116.

The memory 204 may be further configured to store orientation information of a surgical instrument that is utilized to resect a surgical region of interest in a surgical cavity, with respect to a vertical reference axis. The memory 204 may be further configured to store operating systems and associated applications. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The network interface 206 may comprise suitable logic, circuitry, and interfaces that may be configured to communicate with the plurality of medical imaging devices 104, the surgical image capture device 106, the medical data server 108, and/or the display screen 110, via the communication network 112 (as shown in FIG. 1). The network interface 206 may implement known technologies to support wired or wireless communication of the surgical assistive device 102 with the communication network 112. The network interface 206 may include, but is not limited to, an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer.

The I/O device 208 may comprise suitable logic, circuitry, and interfaces that may be configured to receive an input from and provide an output to a user based on the received input from the user. The I/O device 208 may receive an input from the surgical image capture device 106 and provide an output to the display screen 110. The I/O device 208 may be coupled to the surgical image capture device 106 and the display screen 110 through dedicated buses and/or channels. Examples of the input devices may include, but are not limited to, the surgical image capture device 106, a touch screen, a camera, a keyboard, a mouse, a joystick, a microphone, a motion sensor, a light sensor, and/or a docking station. Examples of the output devices may include, but are not limited to, the display screen 110, a projector screen, and/or a speaker.

The processor 210 may comprise suitable logic, circuitry, and interfaces that may be configured to execute a set of instructions stored in the memory 204. Examples of the processor 210 may be an x86-based processor, x86-64-based processor, an ASIC processor, a CPU, an EPIC processor, a VLIW processor, and/or other processors or circuits.

Figure 3A:
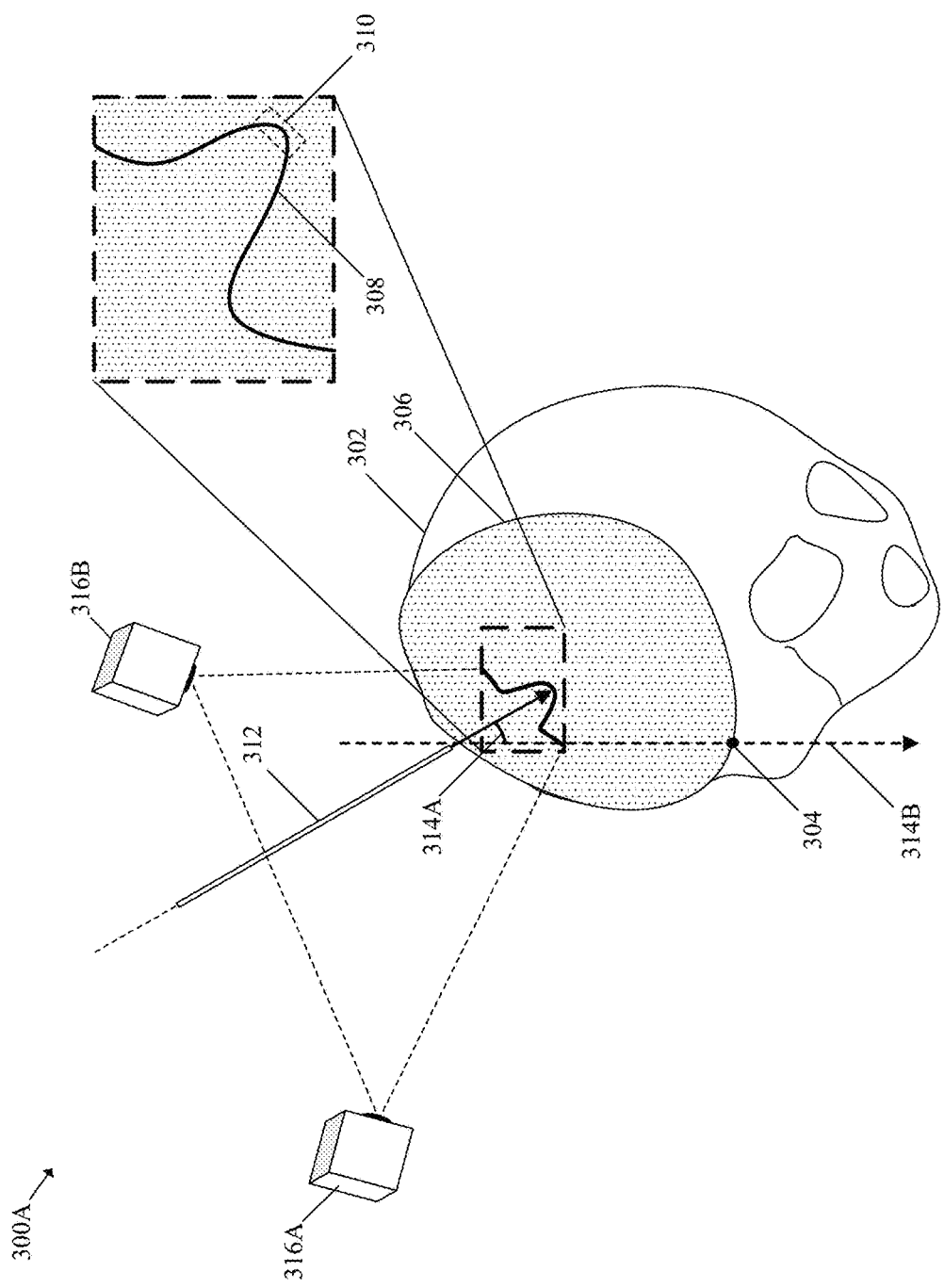
FIG. 3A is a scenario that illustrates a view of the brain affected by intraoperative shifts caused by deformations of an anatomical portion of the brain, in accordance with an embodiment of the disclosure.
Figure 3B:
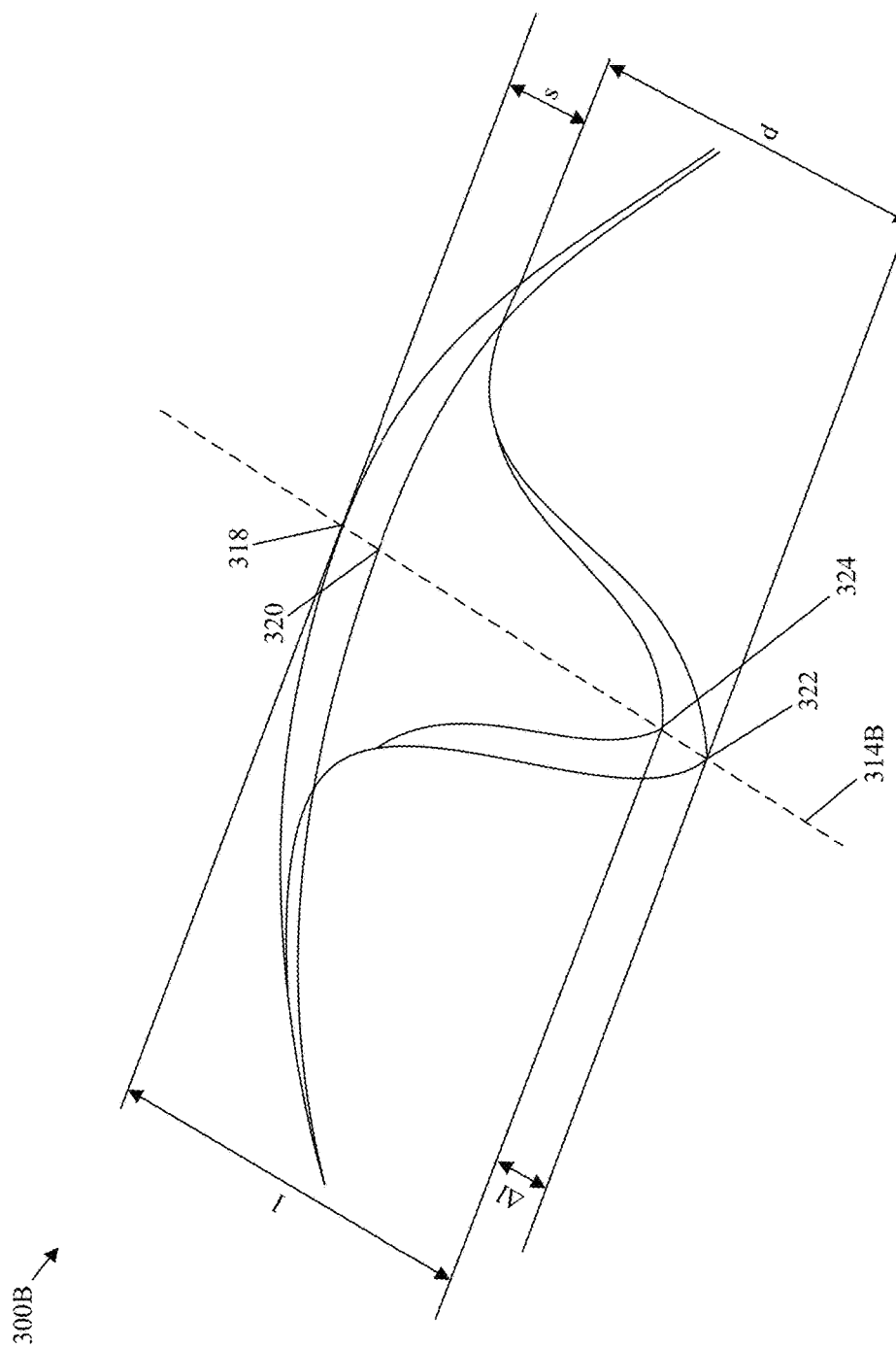
FIG. 3B illustrates a representative view of an anatomical portion of the brain to depict estimation of an intraoperative brain shift caused by deformations of the anatomical portion of the brain, in accordance with an embodiment of the disclosure.

The operations executed by the processor 210 have been described in FIGS. 3A and 3B with an example of a brain of the human subject 116 as the anatomical portion 114 of interest. Notwithstanding, the anatomical portion 114 may also be other anatomical portions of the human subject 116, without limiting the scope of the disclosure.

FIG. 3A is a scenario that illustrates a view of the brain affected by intraoperative shifts caused by deformations of an anatomical portion of the brain, in accordance with an embodiment of the disclosure. FIG. 3A is explained in conjunction with elements from FIG. 1 and FIG. 2. With reference to FIG. 3A, there is shown an intraoperative view 300A of the brain within a skull 302 that is cut open in the intraoperative stage. The intraoperative view 300A includes the skull 302 of the human subject 114, a reference point 304, and an anatomical portion 306 exposed after an incision into the skull 302, a surgical cavity 308 in the anatomical portion 306, and a surgical region of interest 310. There is also shown a surgical instrument 312, an angle 314A that indicates an orientation of the surgical instrument 312, a vertical reference axis 314B along which the weight of the brain is exerted, a stereo microscope 316A and a stereo microscope 316B at known locations around the anatomical portion 306.

The reference point 304 may act as a reference location for the anatomical portion 306 and a location of the reference point 304 is invariant throughout a preoperative stage and an intraoperative stage of the surgery. The reference point 304 may be further utilized to register a reconstructed 3D graphic model of the brain after an intraoperative shift is determined by the surgical assistive device 102, in an event where tissue deformation occurs along with a loss of cerebrospinal fluid.

The anatomical portion 306 may be a defined portion of the brain exposed to the surgical image capture device 106 (e.g., the stereo microscope 316A and the stereo microscope 316B) post an incision of the skull 302. In surgery, the incision in the skull 302 may be performed by the surgeon 118 based on the reference point 304 and a known location of the surgical region of interest 310 (e.g., a region associated with a tumor or an abnormal growth) identified from the pre-operative images of the human subject 114. A tissue, such as a malignant cancer tissue, may require a resection from the surgical cavity 308 of the anatomical portion 306. The tissue may be present in the surgical region of interest 310 of the surgical cavity 308. The surgical instrument 312 may be further guided, by the surgeon 118, to a bottom of the surgical cavity 308 where the tissue is present. Thereafter, the tissue present in the anatomical portion 306 may be removed by the surgeon 116 using the surgical instrument 312. After incision into the skull 302, the brain may no longer hold the cerebrospinal fluid held around the tissues in the anatomical portion 306 and therefore, the brain or more specifically, the anatomical portion 306 may deform due to a loss of the fluid, and influence of gravity.

The anatomical portion 306 may undergo an initial positional shift due to sudden loss of the fluid and apparent deformation of the anatomical portion 306 after the incision into the skull 302. While the brain is in the intraoperative state, the anatomical portion 306 may undergo deformation and therefore, due to an intraoperative brain shift, the location of the tissue may change. Therefore, the estimation of the intraoperative brain shift (also referred to as a residual shift) may be required. Also, in some cases, earlier known location(s) of the tissue in the anatomical portion 306 may further need an update to reconstruct 3D graphic models of the brain (or the anatomical portion 306) in the intraoperative state.

In surgery, the surgical instrument 312 may be utilized by the surgeon 116, to resect a tissue in the surgical region of interest 310 of the surgical cavity 308, with respect to the vertical reference axis 314B. The vertical reference axis 314B may correspond to a direction along which the weight of the anatomical portion 306 is exerted. The surgical instrument 312 makes the angle 314A (represented by "θ") with respect to the vertical reference axis 314B. The angle 314A may be part of orientation information of the surgical instrument 312 during the surgery. The orientation information of the surgical instrument 312 and the material properties of different tissues in the anatomical portion 306 may also affect the deformation of the anatomical portion 306 during the surgery.

The processor 210 may be configured to retrieve the material properties of the brain from the memory 204 of the surgical assistive device or directly from the medical data server 108. The material properties may be processed by the processor 210, by taking into account the material parameters associated with a type of tissue (e.g., characterized by neuronal and neuroglia components, etc.) that is exposed after the incision into the protective portion (e.g., the skull 302). The material parameters may include, but are not limited to, tensile elasticity values for a type of tissue in the anatomical portion 306 and a tissue density (e.g., Young's modulus) associated with the type of tissue. The type of tissue in the anatomical portion 306 of the brain may include, but are not limited to grey matter, white matter, nerve tissues and tumor tissues.

The processor 210 may be further configured to retrieve, from the memory 204 of the surgical assistive device 102, orientation information of the surgical instrument 312. The orientation information may be retrieved at a time when the surgical instrument 312 is guided in the surgical cavity 308, for resection of a tissue in the surgical region of interest 310. Also, the orientation information is determined with respect to the vertical reference axis 314B. The values of the orientation information of the surgical instrument 312 may be further implemented in application of a first relationship model and a second relationship model for estimations of a residual shift (or the intraoperative brain shift) of the anatomical portion 306. The details of estimation of the intraoperative brain shift has been further described in detail in FIG. 3B.

FIG. 3B illustrates a representative view of an anatomical portion of the brain to depict estimation of an intraoperative brain shift caused by deformations of the anatomical portion of the brain, in accordance with an embodiment of the disclosure. FIG. 3B is explained in conjunction with elements from FIGS. 1, 2, and 3A. With reference to FIG. 3B, there is shown a representative view 300B of the anatomical portion 306 and the surgical cavity 308, both of which suffer an intraoperative brain shift caused by a tissue deformation and loss of cerebrospinal fluid during surgery.

In the representative view 300B, there is shown a first position 318 of an anatomical surface of the anatomical portion 306 and a second position 320 of the anatomical surface. The first position 318 is obtained prior to an incision into the skull 302 and the second position 320 is obtained post the incision into the skull 302. There is also shown an apparent position 322 and a real position 324 of the surgical region of interest 310 in the surgical cavity 308. The apparent position 322 may be initially estimated at a first depth value (represented by "d") with respect to the second position 320 and the real position 324 may be further estimated at a second depth value (represented by "l") with respect to the first position 318. The difference in the first position 318 and the second position 320 may be the initial positional shift (represented by "s") and a difference in the first depth value (d) and the second depth value (l) may be a residual shift (also represented by "al").

The surgical image capture device 106 (e.g., the stereo microscope 316A and the stereo microscope 316B at known locations) may be configured to capture a plurality of stereo images of the anatomical portion 306 (i.e., a portion of brain in this case). The surgical image capture device 106 may be a digital stereoscopic microscope that is affixed to a precision stereoscopic camera. The surgical assistive device 102 may be configured to determine the initial positional shift (s) of the anatomical surface of the anatomical portion 306, caused by the incision into the protective portion (i.e., the skull 302), from the first position 318 to the second position 320. The first position 318 may correspond to a pre-operative brain surface (i.e., the anatomical surface) of the anatomical portion 306. Similarly, the second position 320 may correspond to intraoperative brain surface (i.e., the anatomical surface) of the anatomical portion 306 after the loss of the cerebrospinal fluid after opening of the skull during surgery.

The initial positional shift (s) may be determined based on comparison of a pre-operative depth value associated with anatomical surface at the first position 318 in pre-operative multimodal images of the brain with a corresponding depth value of the anatomical surface at the second position 320, estimated from the captured plurality of stereo images. The initial positional shift (s) may only contribute up to a fraction of the overall intraoperative brain shift (i.e., the residual shift ($\Delta l$)). As the deformation of the anatomical portion 306 may be non-linear, therefore, some part of the anatomical portion 306 may deform more and some part may deform less. From the representative view 300B, the residual shift ($\Delta l$) may be represented by a polynomial equation (1), as follows:

$$\Delta l = s + d - 1 \quad (1)$$

The surgical assistive device 102 may be further configured to estimate the first depth value (d) from the second position 320 of the anatomical surface to the surgical region of interest 310 present at a bottom of the surgical cavity 308 in the anatomical portion 306. The first depth value (d) may be an apparent depth estimated based on the plurality of stereo images that are captured from different specified positions of the surgical image capture device 106 (e.g., the stereo microscope 316A and the stereo microscope 316B at known locations) to capture views of the anatomical surface of the anatomical portion 306, via an opening caused by the incision.

The surgical assistive device 102 may be further configured to determine the residual shift ($\Delta l$) in a position of the surgical region of interest 310 with respect to the estimated first depth value (d). The residual shift ($\Delta l$) may be determined based on a first relationship model of material parameters (associated with a type of tissue in the anatomical portion 306) and the estimated first depth value (d). The residual shift ($\Delta l$) may be determined such that a deviation in the estimation of the first depth value (d) is compensated by the determined residual shift ($\Delta l$) with respect to the second depth value (l) of the surgical region of interest 310 in the surgical cavity 308.

The residual shift ($\Delta l$) may be determined based on the first relationship model, which may be derived by the surgical assistive device 102, based on a polynomial expansion of a multivariate relationship among at least the material parameters, the determined initial positional shift (s) of the anatomical surface, the orientation information associated with the surgical instrument 312, and the estimated first depth value (d). The first relationship model may be based on a quadratic relationship of the retrieved orientation information, the material parameters of a type of tissue in the anatomical portion 306, and the estimated first depth value (d). The first relationship model is represented by an equation (2), as follows:

$$\Delta l \approx \frac{kd^2}{\mu} \quad (2)$$

where the value of k is a constant for a given value of tissue density (p), an acceleration due to gravity (g) and the angle 314A, and p represents the Young's modulus for a type of tissue in the surgical region of interest 310. "k" is given by an equation (3), as follows:

$$k = \rho \times (g \cos \theta) \quad (3)$$

The first relationship model may be also derived from a second relationship model, which may be further utilized to derive different possibilities for deformation and associated intraoperative brain shifts. The second relationship model may be obtained by a polynomial expansion of a multivariate relationship among the material parameters of a tissue related to the anatomical portion 306, the determined initial positional shift (s), the orientation information associated with the surgical instrument 312, and the estimated first depth value (d). In certain embodiments, the surgical assistive device 102 may be further configured to retrieve, from the memory 204, material parameters associated with the type of tissue that is exposed after the incision in the anatomical portion 306. The material parameters may include tensile elasticity values for the type of tissue in the anatomical portion 306 and a tissue density (p) associated with a type of tissue (e.g., gray matter. white matter, tumorous tissues, etc.). The tensile elasticity values may correspond to Young's modulus (p) that depicts an elastic property of a type of tissue in the anatomical portion 306.

The second relationship model is represented by equations (4), (5), and (6), as follows:

$$l = \frac{-\mu + ks + (\mu + ks)\sqrt{1 + \frac{4k\mu d}{(\mu + ks)^2}}}{2k} \quad (4)$$

$$l = s + \frac{\mu d}{\mu + ks} - \frac{k(\mu d)^2}{(\mu + ks)^3} + O\left(\left(\frac{k\mu d}{(\mu + ks)^2}\right)^3\right) \quad (5)$$

In case, the tissue in the surgical region of interest 310 is a stiff tissue, the Young's modulus ($\mu$) for the tissue may be significantly greater than a product of the constant (k) and the initial positional shift (s). Therefore, in such cases, equation (5) reduces to an equation (6), as follows:

$$l \approx s + d - \frac{kd^2}{\mu} \quad (6)$$

In accordance with an embodiment, on comparison of equation (1) and (2) with (6), equation (2) may also be derived. Equation (2) may be utilized as the first relationship model to determine the residual shift ($\Delta l$), which is given by a quadratic relationship of the constant (k), the first depth value (d) and the Young's modulus (p) of the tissue in the surgical region of interest 310. Equation (6) may be derived after an approximation of an indefinite number of terms in the polynomial expansion of equation (5). In the approximation, therefore, only the first three terms (e.g., $s + (\mu d/\mu + ks) - k(\mu d)^2/(\mu + ks)^3$) of equation (5) may be taken and the remaining terms (e.g., $O((k\mu d)/(\mu + ks)^2)^3$) may be ignored. The surgical assistive device 102 may be configured to utilize the second relationship model (represented by equation (6) to determine the second depth value (l) of the surgical region of interest 310 in the surgical cavity 308 of the anatomical portion 306, with respect to the first position 318 of the anatomical surface.

After the residual shift ($\Delta l$) is determined, the surgical assistive device 102 may be further configured to generate a three dimensional (3D) graphic model of the anatomical portion 306. The 3D graphic model may be generated based on the determined initial positional shift (s) of the anatomical surface, the estimated first depth value (d), the determined residual shift (Δl), and the determined second depth value (l) of the surgical region of interest 310 in the surgical cavity 308.

The surgical assistive device 102 may be further configured to generate surgical guidance information that includes an amount of depth that should be compensated from the first depth value (d) to the second depth value (l), to indicate a correct depth of the surgical region of interest 310 in the surgical cavity 308. The surgical guidance information may be also generated based on the determined residual shift (Δl).

The surgical assistive device 102 may be configured to control display of the generated surgical guidance information on the display screen 110 coupled to the surgical assistive device 102. The display of the generated surgical guidance information may be controlled such that a navigation of a surgical instrument 312 to the surgical region of interest 310 at the second depth value (l) inside the surgical cavity 308 is facilitated. Thereafter, the surgical assistive device 102 may be further configured to update the display of the generated 3D graphic model and the surgical guidance information in real time or near-real time. In other words, the display may be updated in accordance with real time or a near-real time change in the estimation of the first depth value (d), the residual shift (Δl), and the second depth value (l) of the surgical cavity 308. In accordance with an embodiment, the surgical assistive device 102 may be further configured to continuously control rendering of the 3D graphic model of the anatomical portion 306, at the display screen 110. This facilitates a continuous and simplified navigation of the surgical instrument 312 to the surgical region of interest 310 at the second depth value (l) in the surgical cavity 308. The surgical guidance information may be further generated based on the generated 3D graphic model of the anatomical portion 306.

Figure 4A:
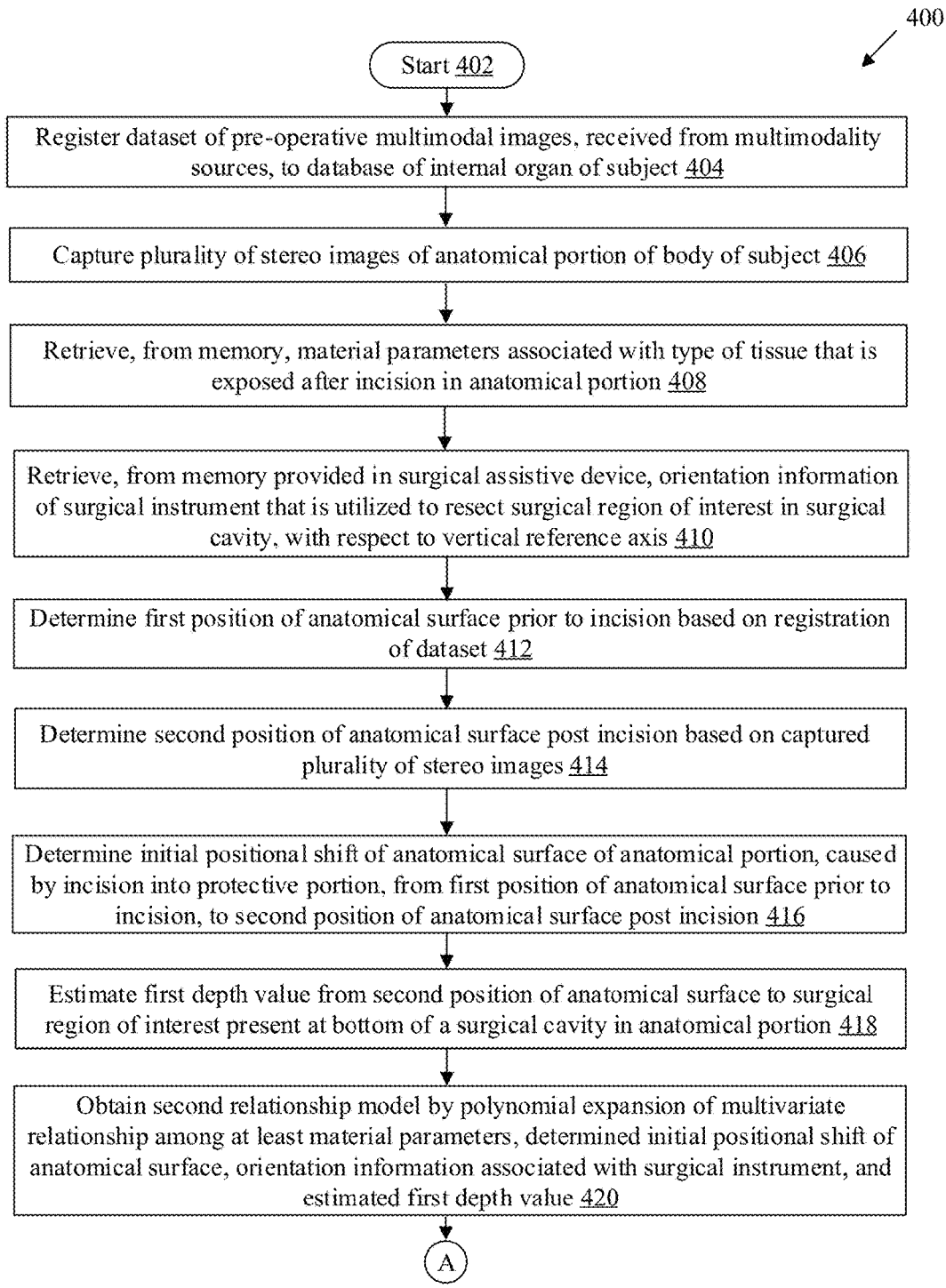
FIG. 4A and FIG. 4B, collectively illustrate a flow chart that depicts exemplary operations for assistance in surgery of anatomical portions of an internal organ, which is affected by an intraoperative shift, in accordance with an embodiment of the disclosure.
Figure 4B:
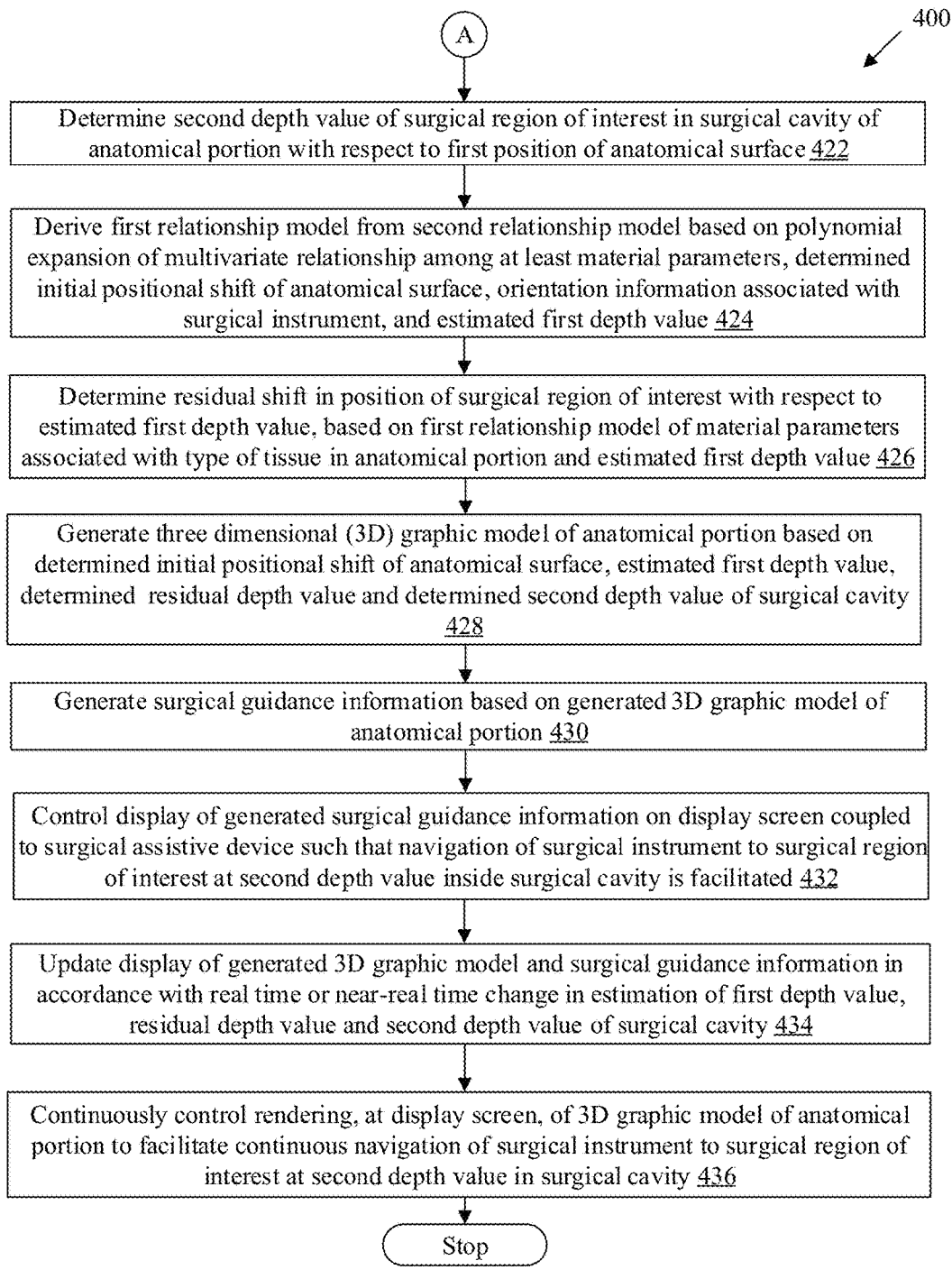

FIGS. 4A and 4B, collectively illustrate a flow chart that depicts exemplary operations for assistance in surgery of anatomical portions of an internal organ, which is affected by an intraoperative shift, in accordance with an embodiment of the disclosure. With reference to FIGS. 4A and 4B, there is shown a flowchart 400. The flowchart 400 is described in conjunction with elements from FIGS. 1, 2, 3A, and 3B. The method, in accordance with the flowchart 400, may be implemented in the surgical assistive device 102. The method starts at 402 and proceeds to 404.

At 404, one or more datasets associated with the anatomical portion 114 may be registered to a database of internal organ of the human subject 116. The one or more datasets may include pre-operative multimodal images of the anatomical portion 114 (or the entire internal organ) of the human subject 116. The registration may be done to visually model the anatomical portion of the internal organ in the intraoperative stage, i.e., during surgery, or to locate a surgical region of interest in the anatomical portion prior to the surgery. The surgical assistive device 102 may be configured to register one or more datasets associated with the anatomical portion 114 to a database of internal organ of the human subject 116.

At 406, a plurality of stereo images of an anatomical portion 114 of a body of a human subject 116 may be captured. The surgical image capture device 106 may be configured to capture a plurality of stereo images of an anatomical portion 114 of a body of the human subject 116. The plurality of stereo images that may be captured from different specified positions of the surgical image capture device 106 to capture views of the anatomical surface of the anatomical portion 114 through the incision.

At 408, material parameters associated with the type of tissue that is exposed after the incision in the anatomical portion 114 may be retrieved from the memory 204. The surgical assistive device 102 may be configured to retrieve, from the memory 204, material parameters associated with the type of tissue that is exposed after the incision in the anatomical portion 114. The material parameters may include tensile elasticity values for the type of tissue in the anatomical portion 114 and a tissue density associated with the type of tissue.

At 410, orientation information of a surgical instrument with respect to a vertical reference axis in a surgical cavity, may be retrieved from the memory 204 of the surgical assistive device 102 that is utilized to resect a surgical region of interest in the surgical cavity. The surgical assistive device 102 may be configured to retrieve the orientation information of a surgical instrument that is utilized to resect a surgical region of interest in a surgical cavity, with respect to a vertical reference axis.

At 412, a first position of the anatomical surface prior to the incision may be determined based on the registration of the dataset. The processor 210 may be further configured to determine the first position of the anatomical surface prior to the incision based on the registration of the dataset.

At 414, a second position of the anatomical surface post the incision may be determined based on the captured plurality of stereo images. The processor 210 may be further configured to determine the second position of the anatomical surface post the incision based on the captured plurality of stereo images.

At 416, an initial positional shift may be determined based on comparison of a pre-operative depth value associated with anatomical surface at the first position in pre-operative multimodal images of the brain with a corresponding depth value of the anatomical surface at the second position. The processor 210 may be configured to determine an initial positional shift based on comparison of a pre-operative depth value, associated with an anatomical surface at the first position in pre-operative multimodal images of the brain, with a corresponding depth value of the anatomical surface at the second position.

At 418, a first depth value may be estimated from the second position of the anatomical surface to a surgical region of interest present at a bottom of a surgical cavity in the anatomical portion 114. The processor 210 may be configured to estimate the first depth value from the second position of the anatomical surface to a surgical region of interest present at a bottom of a surgical cavity in the anatomical portion 114. The first depth value may be an apparent depth estimated based on the plurality of stereo images that are captured from different specified positions of the surgical image capture device 106, to capture views of the anatomical surface of the anatomical portion 114 through the incision. The estimation of the first depth value is shown and described, for example, in FIG. 3B.

At 420, a second relationship model may be obtained by a polynomial expansion of a multivariate relationship among at least the material parameters, the determined initial positional shift of the anatomical surface, the orientation information associated with the surgical instrument, and the estimated first depth value. The processor 210 may be configured to obtain a second relationship model by a polynomial expansion of a multivariate relationship among at least the material parameters, the determined initial positional shift of the anatomical surface, the orientation information associated with the surgical instrument, and the estimated first depth value.

At 422, a second depth value may be determined of the surgical region of interest in the surgical cavity of the anatomical portion 114 with respect to the first position of the anatomical surface. The processor 210 may be configured to determine the second depth value of the surgical region of interest in the surgical cavity of the anatomical portion 114 with respect to the first position of the anatomical surface. The second depth value may be determined based on a second relationship model that is obtained by a polynomial expansion of a multivariate relationship among at least the material parameters, the determined initial positional shift of the anatomical surface, orientation information associated with the surgical instrument, and the estimated first depth value. The determination of the second depth value is shown and described, for example, in line diagram 3B.

At 424, a first relationship model may be derived from the second relationship model based on a polynomial expansion of a multivariate relationship among at least the material parameters, the determined initial positional shift of the anatomical surface, orientation information associated with the surgical instrument, and the estimated first depth value. The first relationship model may be based on a quadratic relationship of the retrieved orientation information, the material parameters of the type of tissue, and the estimated first depth value. The processor 210 may be configured to derive the first relationship model from the second relationship model.

At 426, a residual shift may be determined in a position of the surgical region of interest with respect to the estimated first depth value. The processor 210 may be configured to determine the residual shift in a position of the surgical region of interest with respect to the estimated first depth value. The determination of the residual shift may be based on the first relationship model of material parameters associated with a type of tissue in the anatomical portion 114 and the estimated first depth value. The residual shift may be determined such that a deviation in the estimation of the first depth value, caused by tissue deformation in the anatomical portion 114, is compensated by the determined residual shift with respect to a second depth value of the surgical region of interest in the surgical cavity.

At 428, a three dimensional (3D) graphic model of the anatomical portion 114 may be generated. The processor 210 may be configured to generate a three dimensional (3D) graphic model of the anatomical portion 114. The 3D graphic model may be generated based on the determined initial positional shift of the anatomical surface, the estimated first depth value, the determined residual shift, and the determined second depth value of the surgical region of interest in the surgical cavity.

At 430, surgical guidance information may be generated based on the generated 3D graphic model of the anatomical portion 114. The processor 210 may be configured to generate the surgical guidance information that includes an amount of depth that should be compensated from the first depth value to the second depth value, to indicate a correct depth of the surgical region of interest in the surgical cavity. The surgical guidance information may be generated based on the determined residual shift.

At 432, display of the generated surgical guidance information may be controlled on the display screen 110 coupled to the surgical assistive device 102 such that a navigation of a surgical instrument to the surgical region of interest at the second depth value inside the surgical cavity is facilitated. The processor 210 may be configured to control the display of the generated surgical guidance information on the display screen 110 coupled to the surgical assistive device 102 such that a navigation of a surgical instrument to the surgical region of interest at the second depth value inside the surgical cavity is facilitated.

At 434, the display of the generated 3D graphic model and the surgical guidance information may be updated in accordance with a real time or a near-real time change in estimation of the first depth value, the residual shift, and the second depth value of the surgical cavity. The processor 210 may be configured to update a display of the generated 3D graphic model and the surgical guidance information, in accordance with a real time or a near-real time change in estimation of the first depth value, the residual shift, and the second depth value of the surgical cavity.

At 436, rendering, at the display screen 110, of the 3D graphic model of the anatomical portion 114 may be continuously controlled to facilitate a continuous navigation of the surgical instrument to the surgical region of interest at the second depth value in the surgical cavity. The processor 210 may be further configured to continuously control rendering, at the display screen 110, of the 3D graphic model of the anatomical portion 114 to facilitate a continuous navigation of the surgical instrument to the surgical region of interest at the second depth value in the surgical cavity. Control passes to end.

Various embodiments of the disclosure may provide a non-transitory computer readable medium and/or storage medium, and/or a non-transitory machine readable medium and/or storage medium with a machine code and/or a set of instructions stored thereon and executable by a machine and/or a computer to render guidance information that facilitates a surgeon to compensate for an intraoperative shift (i.e., a residual shift) in deformation of anatomical portion of an internal organ of a subject. The surgeon may compensate for the intraoperative shift by moving a surgical instrument at a correct depth inside a surgical cavity within an anatomical portion. The set of instructions may be executable by the machine and/or the computer to perform the steps that comprise the capture of plurality of stereo images of the anatomical portion of the subject. The material parameters associated with a type of tissue that may be exposed after incision in anatomical portion may be retrieved from the memory. A dataset of pre-operative multimodal images of the anatomical portion of the internal organ of the subject may be registered from the medical data server. The surgical orientation information of a surgical instrument that may be utilized to resect a surgical region of interest may be retrieved with respect to vertical reference axis. An initial positional shift of an anatomical surface of the anatomical portion that is caused by the incision into the protective portion, may be determined from a first position of the anatomical surface (prior to the incision) to a second position of the anatomical surface (post the incision). A first depth value may be estimated for a surgical surface at a bottom of a surgical cavity in the anatomical portion with respect to the second position of the anatomical surface. The first depth value may be estimated based on the captured plurality of stereo images from the different position values. A residual shift may be estimated in a position of the surgical surface with respect to the estimated first depth value, based on a first relationship model of material parameters associated with a type of tissue in the anatomical portion and the estimated first depth value. The residual shift may be estimated such that a deviation in the estimation of the first depth value, caused by tissue deformation of the surgical surface, is compensated by the estimated residual shift with respect to a second depth value of the surgical surface in the surgical cavity. Surgical guidance information may be displayed to facilitate navigation of the surgical instrument to the second depth value of the surgical surface inside the surgical cavity.

Exemplary aspects of the disclosure may include a surgical assistive device (such as the surgical assistive device 102) that includes a surgical image capture device (such as the surgical image capture device 106) configured to capture a plurality of stereo images of an anatomical portion (such as the anatomical portion 114) of a body of a subject, from different position values of the surgical image capture device. The anatomical portion may be a defined portion of an internal organ exposed to the surgical image capture device post an incision of a protective portion that encloses the internal organ. The surgical assistive device may further include a circuitry (such as the compensation circuitry 202) configured to determine an initial positional shift of an anatomical surface of the anatomical portion, caused by the incision into the protective portion, from a first position of the anatomical surface prior to the incision to a second position of the anatomical surface post the incision. The shift compensation circuitry may be configured to estimate a first depth value for a surgical surface at a bottom of a surgical cavity in the anatomical portion with respect to the second position of the anatomical surface. The first depth value may be estimated based on the captured plurality of stereo images from the different position values. The shift compensation circuitry may be configured to estimate a residual shift in a position of the surgical surface with respect to the estimated first depth value. The estimation of the residual shift may be based on a first relationship model of material parameters associated with a type of tissue in the anatomical portion and the estimated first depth value. The residual shift may be estimated such that a deviation in the estimation of the first depth value, caused by tissue deformation of the surgical surface, may be compensated by the estimated residual shift with respect to a second depth value of the surgical surface in the surgical cavity. The shift compensation circuitry may be further configured to display surgical guidance information to facilitate navigation of a surgical instrument to the second depth value of the surgical surface inside the surgical cavity.

In accordance with an embodiment, the initial positional shift may be determined based on comparison of a depth value associated with anatomical surface at the first position in pre-operative multimodal images of the internal organ with a corresponding depth value of the anatomical surface at the second position, estimated from the captured plurality of stereo images. The surgical image capture device may be a digital stereoscopic microscope that is affixed to a precision stereoscopic camera.

The anatomical portion may be a portion of the brain that is exposed after incision of the skull that encloses the portion of the brain. The surgical surface may be at least a brain tissue, a network of blood vessels, and brain ventricles present in the anatomical portion. The type of tissue in the portion of the brain may be at least one of a gray matter, a white matter, and a tumor.

In accordance with an embodiment, the compensation circuitry may be further configured to retrieve the material parameters associated with the type of tissue that is exposed after the incision in the anatomical portion. The tissue material parameters may include at least one of a young's modulus of the type of tissue in the anatomical portion and a tissue density associated with the type of tissue. The compensation circuitry may be further configured to retrieve orientation information of the surgical instrument that may be utilized for a resection of the surgical surface in the surgical cavity, with respect to a vertical reference axis.

In accordance with an embodiment, the first relationship model may be based on a quadratic relationship of the retrieved orientation information, the material parameters of the type of tissue, and the estimated first depth value. The compensation circuitry may be further configured to estimate the second depth value of the surgical surface in the surgical cavity of the anatomical portion with respect to the first position of the anatomical surface. The second depth value may be estimated based on a second relationship model that may be obtained by a polynomial expansion of a multivariate relationship among at least the material parameters, the determined initial positional shift of the anatomical surface, orientation information associated with the surgical instrument, and the estimated first depth value.

In accordance with an embodiment, the compensation circuitry may be further configured to derive the first relationship model from the second relationship model. Such derivation of the first relationship model from the second relationship model may be based on the polynomial expansion of the multivariate relationship among at least the material parameters, the determined initial positional shift of the anatomical surface, orientation information associated with the surgical instrument, and the estimated first depth value.

In accordance with an embodiment, the compensation circuitry may be further configured to register a dataset of pre-operative multimodal images of the internal organ received from multimodality sources. The compensation circuitry may be configured to determine the first position of the anatomical surface prior to the incision based on the registration of the dataset.

In accordance with an embodiment, the compensation circuitry may be further configured to generate a three dimensional (3D) graphic model of the anatomical portion based on the determined initial positional shift of the anatomical surface, the estimated first depth value, the estimated residual shift and the second depth value of the surgical cavity. The compensation circuitry may be further configured to update a display of the generated 3D graphic model and the surgical guidance information in accordance with real time changes in estimation of the first depth value, the residual shift, and the second depth value of the surgical cavity. The compensation circuitry may be further configured to control a rendering, at a display device, of the 3D graphic model of the anatomical portion to facilitate a continuous navigation of the surgical instrument to the second depth value in a region of interest in the surgical cavity. In some embodiments, the compensation circuitry may be further configured to generate the surgical guidance information based on the generated 3D graphic model of the anatomical portion.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein.

The present disclosure may be realized in hardware that comprises a portion of an integrated circuit that also performs other functions.

The present disclosure may also be embedded in a computer program product, which comprises all the features that enable the implementation of the methods described herein, and which when loaded in a computer system is able to carry out these methods. Computer program, in the present context, means any expression, in any language, code or notation, of a set of instructions intended to cause a system that has an information processing capability to perform a particular function either directly, or after either or both of the following: a) conversion to another language, code or notation; b) reproduction in a different material form.

While the present disclosure has been described with reference to certain embodiments, it will be understood by those skilled in the art that various changes may be made and equivalents may be substituted without departure from the scope of the present disclosure. In addition, many modifications may be made to adapt a particular situation or material to the teachings of the present disclosure without departure from its scope. Therefore, it is intended that the present disclosure not be limited to the particular embodiment disclosed, but that the present disclosure will include all embodiments that falls within the scope of the appended claims.

What is claimed is:

1. A surgical assistive device, comprising:
   a surgical image capture device, wherein the surgical image capture device is configured to capture a plurality of stereo images of an anatomical portion of a body of a subject, wherein the anatomical portion is a defined portion of an internal organ exposed to the surgical image capture device post an incision of a protective portion that encloses the internal organ; and
   compensation circuitry configured to:
      determine an initial positional shift of an anatomical surface of the anatomical portion, caused by the incision into the protective portion, from a first position of the anatomical surface prior to the incision to a second position of the anatomical surface post the incision, wherein the initial positional shift is determined based on comparison of a pre-operative depth value associated with the anatomical surface at the first position in pre-operative multimodal images of the internal organ with a corresponding depth value of the anatomical surface at the second position, estimated from the captured plurality of stereo images;
      estimate a first depth value from the second position of the anatomical surface to a surgical region of interest present at a bottom of a surgical cavity in the anatomical portion, wherein the first depth value is an apparent depth estimated based on the plurality of stereo images that are captured from different specified positions of the surgical image capture device, to capture views of the anatomical surface of the anatomical portion through the incision;
      determine a residual shift in a position of the surgical region of interest with respect to the estimated first depth value, based on a first relationship model of material parameters associated with a type of tissue in the anatomical portion and the estimated first depth value, wherein the residual shift is determined such that a deviation in the estimation of the first depth value, caused by tissue deformation in the anatomical portion, is compensated by the determined residual shift with respect to a second depth value of the surgical region of interest in the surgical cavity;
      generate surgical guidance information that comprises an amount of depth that is compensated from the first depth value to the second depth value, to indicate a correct depth of the surgical region of interest in the surgical cavity, based on the determined residual shift; and
      control display of the generated surgical guidance information on a display screen coupled to the surgical assistive device such that a navigation of a surgical instrument to the surgical region of interest at the second depth value inside the surgical cavity is facilitated.

2. The surgical assistive device according to claim 1, wherein the surgical image capture device is a digital stereoscopic microscope that is affixed to a precision stereoscopic camera.

3. The surgical assistive device according to claim 1, wherein the anatomical portion is a brain portion that is exposed after incision of a skull that corresponds to the protective portion that encloses the brain portion, and the surgical region of interest is at least a brain tissue, a network of blood vessels, and brain ventricles present in the anatomical portion.

4. The surgical assistive device according to claim 3, wherein the type of tissue in the brain portion is at least one of a gray matter, a white matter, and a tumor.

5. The surgical assistive device according to claim 1, further comprises a memory, wherein the compensation circuitry is further configured to retrieve material parameters associated with the type of tissue that is exposed after the incision in the anatomical portion from the memory, and wherein the material parameters comprises tensile elasticity values for the type of tissue in the anatomical portion and a tissue density associated with the type of tissue.

6. The surgical assistive device according to claim 1, wherein the compensation circuitry is further configured to retrieve, from a memory provided in the surgical assistive device, orientation information of the surgical instrument that is utilized to resect the surgical region of interest in the surgical cavity, with respect to a vertical reference axis.

7. The surgical assistive device according to claim 6, wherein the first relationship model is based on a quadratic relationship of the retrieved orientation information, the material parameters of the type of tissue, and the estimated first depth value.

8. The surgical assistive device according to claim 1, wherein the compensation circuitry is further configured to determine the second depth value of the surgical region of interest in the surgical cavity of the anatomical portion with respect to the first position of the anatomical surface.

9. The surgical assistive device according to claim 1, wherein the second depth value is determined based on a second relationship model that is obtained by a polynomial expansion of a multivariate relationship among at least the material parameters, the determined initial positional shift of the anatomical surface, orientation information associated with the surgical instrument, and the estimated first depth value.

10. The surgical assistive device according to claim 9, wherein the compensation circuitry is further configured to derive the first relationship model from the second relationship model based on a polynomial expansion of a multivariate relationship among at least the material parameters, the determined initial positional shift of the anatomical surface, the orientation information associated with the surgical instrument, and the estimated first depth value.

11. The surgical assistive device according to claim 1, wherein the compensation circuitry is further configured to register a dataset of the pre-operative multimodal images, received from multimodality sources, to a database for the internal organ of the subject.

12. The surgical assistive device according to claim 11, wherein the compensation circuitry is further configured to determine the first position of the anatomical surface prior to the incision based on the registration of the dataset.

13. The surgical assistive device according to claim 1, wherein the compensation circuitry is further configured to generate a three dimensional (3D) graphic model of the anatomical portion based on the determined initial positional shift of the anatomical surface, the estimated first depth value, the determined residual shift, and the determined second depth value of the surgical cavity.

14. The surgical assistive device according to claim 13, wherein the compensation circuitry is further configured to update a display of the generated 3D graphic model and the surgical guidance information in accordance with a real time or a near-real time change in estimation of the first depth value, the residual shift, and the second depth value of the surgical cavity.

15. The surgical assistive device according to claim 14, wherein the compensation circuitry is further configured to continuously control, at the display screen, rendering of the 3D graphic model of the anatomical portion to facilitate a continuous navigation of the surgical instrument to the surgical region of interest at the second depth value in the surgical cavity.

16. The surgical assistive device according to claim 14, wherein the compensation circuitry is further configured to generate the surgical guidance information based on the generated 3D graphic model of the anatomical portion.

17. A method, comprising:
in a surgical assistive device that comprises a surgical image capture device and compensation circuitry:
capturing, by the surgical image capture device, a plurality of stereo images of an anatomical portion of a body of a subject, wherein the anatomical portion is a defined portion of an internal organ exposed to the surgical image capture device post an incision of a protective portion that encloses the internal organ;
determining, by the compensation circuitry, an initial positional shift of an anatomical surface of the anatomical portion, caused by the incision into the protective portion, from a first position of the anatomical surface prior to the incision to a second position of the anatomical surface post the incision, wherein the initial positional shift is determined based on comparison of a pre-operative depth value associated with the anatomical surface at the first position in pre-operative multimodal images of the internal organ with a corresponding depth value of the anatomical surface at the second position, estimated from the captured plurality of stereo images;

estimating, by the compensation circuitry, a first depth value from the second position of the anatomical surface to a surgical region of interest present at a bottom of a surgical cavity in the anatomical portion, wherein the first depth value is an apparent depth estimated based on the plurality of stereo images that are captured from different specified positions of the surgical image capture device, to capture views of the anatomical surface of the anatomical portion through the incision;

determining, by the compensation circuitry, a residual shift in a position of the surgical region of interest with respect to the estimated first depth value, based on a first relationship model of material parameters associated with a type of tissue in the anatomical portion and the estimated first depth value, wherein the residual shift is determined such that a deviation in the estimation of the first depth value, caused by tissue deformation in the anatomical portion, is compensated by the determined residual shift with respect to a second depth value of the surgical region of interest in the surgical cavity;

generating, by the compensation circuitry, surgical guidance information that comprises an amount of depth that is compensated from the first depth value to the second depth value, to indicate a correct depth of the surgical region of interest in the surgical cavity, based on the determined residual shift; and controlling, by the compensation circuitry, display of the generated surgical guidance information on a display screen coupled to the surgical assistive device such that a navigation of a surgical instrument to the surgical region of interest at the second depth value inside the surgical cavity is facilitated.

* * * * *